US009662459B2

(12) United States Patent
Hadzic

(10) Patent No.: US 9,662,459 B2
(45) Date of Patent: May 30, 2017

(54) APPARATUS AND METHOD PERTAINING TO THE MONITORING OF INJECTION PRESSURE DURING ADMINISTRATION OF NERVE BLOCKS

(71) Applicant: Admir Hadzic, New York, NY (US)

(72) Inventor: Admir Hadzic, New York, NY (US)

(73) Assignee: B. Braun Melsungen AG, Melsungen (DE)

( * ) Notice: Subject to any disclaimer, the term of this patent is extended or adjusted under 35 U.S.C. 154(b) by 989 days.

(21) Appl. No.: 13/723,611

(22) Filed: Dec. 21, 2012

(65) Prior Publication Data

US 2013/0165904 A1 Jun. 27, 2013

Related U.S. Application Data

(60) Provisional application No. 61/579,919, filed on Dec. 23, 2011.

(51) Int. Cl.
*A61M 1/00* (2006.01)
*A61M 31/00* (2006.01)
*A61M 5/48* (2006.01)

(52) U.S. Cl.
CPC ............. *A61M 5/486* (2013.01); *A61M 5/484* (2013.01); *A61M 5/488* (2013.01)

(58) Field of Classification Search
CPC ....... A61M 5/486; A61M 5/484; A61M 5/488
USPC .................................................. 604/121, 512
See application file for complete search history.

(56) References Cited

U.S. PATENT DOCUMENTS 5,295,967 A * 3/1994 Rondelet ........... A61M 5/16854 128/DIG. 12
6,200,289 B1 * 3/2001 Hochman ........... A61M 5/1456 128/DIG. 12
2003/0225371 A1 * 12/2003 Hadzic .............. A61M 5/16854 604/118
2012/0259406 A1 * 10/2012 Schreck ................. A61B 6/481 623/1.27

* cited by examiner

*Primary Examiner* — Jason Flick
(74) *Attorney, Agent, or Firm* — Fitch Even Tabin & Flannery LLP

(57) ABSTRACT

A control circuit that operably couples to a display and to a nerve block injection pressure sensor provides a display of both a current nerve block injection pressure value and a current nerve block injection pressure categorical range. That categorical range can comprise, for example, one of a plurality of available categorical ranges which may be visually differentiated from one another by color. The control circuit can also detect (and display) a maximum nerve block injection pressure value (and/or calculate a mean nerve block injection pressure value) as corresponds to a given monitored nerve block injection procedure. The control circuit can also detect negative nerve block injection pressure events and identify those events as aspiration events to facilitate keeping a count of aspiration events during the course of a given nerve block injection procedure. The control circuit can also help ensure observe of the proper patient laterality if desired.

14 Claims, 6 Drawing Sheets

905 907 203 903 301 304 18 3 302 309 901 200 904 902 906 900

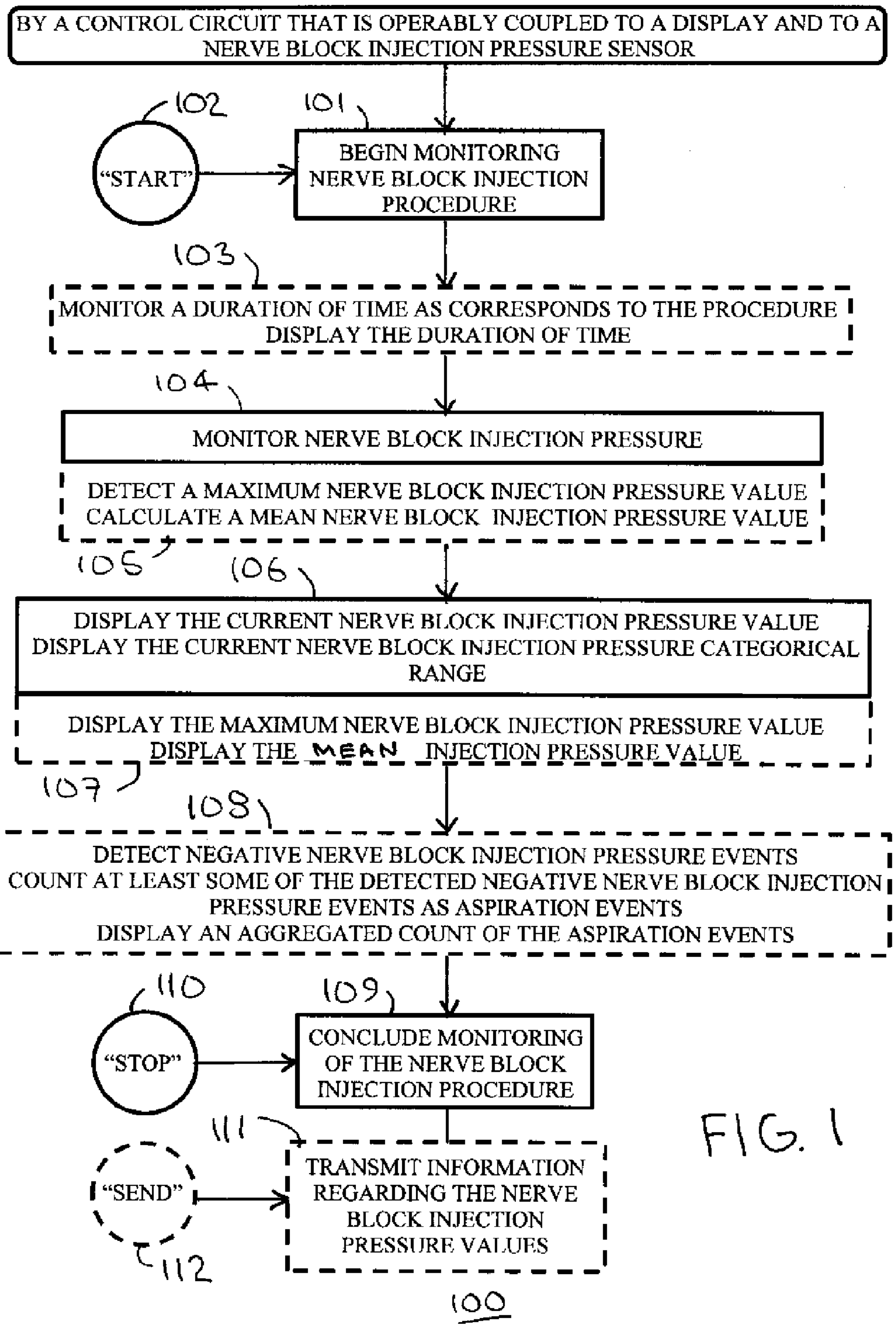
BY A CONTROL CIRCUIT THAT IS OPERABLY COUPLED TO A DISPLAY AND TO A NERVE BLOCK INJECTION PRESSURE SENSOR
102
"START"
101
BEGIN MONITORING NERVE BLOCK INJECTION PROCEDURE
103
MONITOR A DURATION OF TIME AS CORRESPONDS TO THE PROCEDURE
DISPLAY THE DURATION OF TIME
104
MONITOR NERVE BLOCK INJECTION PRESSURE
DETECT A MAXIMUM NERVE BLOCK INJECTION PRESSURE VALUE
CALCULATE A MEAN NERVE BLOCK INJECTION PRESSURE VALUE
105
106
DISPLAY THE CURRENT NERVE BLOCK INJECTION PRESSURE VALUE
DISPLAY THE CURRENT NERVE BLOCK INJECTION PRESSURE CATEGORICAL RANGE
DISPLAY THE MAXIMUM NERVE BLOCK INJECTION PRESSURE VALUE
DISPLAY THE MEAN INJECTION PRESSURE VALUE
107
108
DETECT NEGATIVE NERVE BLOCK INJECTION PRESSURE EVENTS
COUNT AT LEAST SOME OF THE DETECTED NEGATIVE NERVE BLOCK INJECTION PRESSURE EVENTS AS ASPIRATION EVENTS
DISPLAY AN AGGREGATED COUNT OF THE ASPIRATION EVENTS
110
"STOP"
109
CONCLUDE MONITORING OF THE NERVE BLOCK INJECTION PROCEDURE
111
"SEND"
TRANSMIT INFORMATION REGARDING THE NERVE BLOCK INJECTION PRESSURE VALUES
112
100
FIG. 1

MEMORY
202
201
DISPLAY
CONTROL CIRCUIT
204
NERVE BLOCK INJECTION PRESSURE SENSOR
203
206
205
DATA INTERFACE
USER-INPUT INTERFACE

200

APPARATUS AND METHOD PERTAINING TO THE MONITORING OF INJECTION PRESSURE DURING ADMINISTRATION OF NERVE BLOCKS

RELATED APPLICATION(S)

This application claims the benefit of U.S. Provisional application No. 61/579,919 entitled Digital Pressure Monitor For Use When Administering Nerve Blocks, filed Dec. 23, 2011, which is incorporated by reference in its entirety herein.

TECHNICAL FIELD

This invention relates generally to the administration of nerve blocks and more particularly to the monitoring of corresponding nerve block injection pressure.

BACKGROUND

Nerve blocks are known in the art and relate generally to the injection of local anesthetic proximal to one or more specific nerves to provide (usually) anesthesia or temporary control of pain. The anesthetic typically comprises a liquid that the service provider administers via a needle. Such a needle must be properly placed. Administering the anesthetic too far from the nerve can defeat the intended purpose, while contacting or inserting the needle into the nerve or its fascicles can cause nerve injury and harm to the patient.

Many service providers use ultrasonography to help guide the needle to a proper location. Unfortunately, while ultrasonography can help to avoid having the needle too distant from the nerve or impinging directly upon the nerve, ultrasonography cannot in and of itself guarantee a correct and risk-free placement of the needle. For example, ultrasonography alone cannot always guarantee that the needle tip is not disposed within a nerve, nerve fascicles, tendon, or other poorly-compliant spaces.

Accordingly, those skilled in the art often rely upon "feel" of the resistance to injection to help inform the correct placement of the needle during an injection of the medication (typically a local anesthetic solution). In particular, in many cases the abnormally high pressure within a needle incorrectly located in a poorly-compliant tissue informs this hand or syringe "feel." A failure to "feel" an abnormally high resistance or a failure to abort the injection when such high resistance is "felt" can lead to an unrecognized injection into a wrong tissue. In turn, such an injection can result in a failure to accomplish a block or mechanical and injection damage to the injected tissues. Possibly adversely affected tissues and consequences include nerves (nerve damage), tendons (rupture and inefficient block) and blocking the wrong side of the tissue fascia (block failure).

Mechanical pressure monitors are also known in the art that can provide a general visual indication as to whether the current pressure in the needle is generally within a useful nominal range, below that useful nominal range, or above that useful nominal range.

Again, however, existing approaches in these regards are not sufficient to meet all user needs in all application settings.

BRIEF DESCRIPTION OF THE DRAWINGS

The above needs are at least partially met through provision of the apparatus and method pertaining to the monitoring of nerve block injection pressure described in the following detailed description, particularly when studied in conjunction with the drawings, wherein:

FIG. 1 comprises a flow diagram as configured in accordance with various embodiments of the invention;

Figure 2:
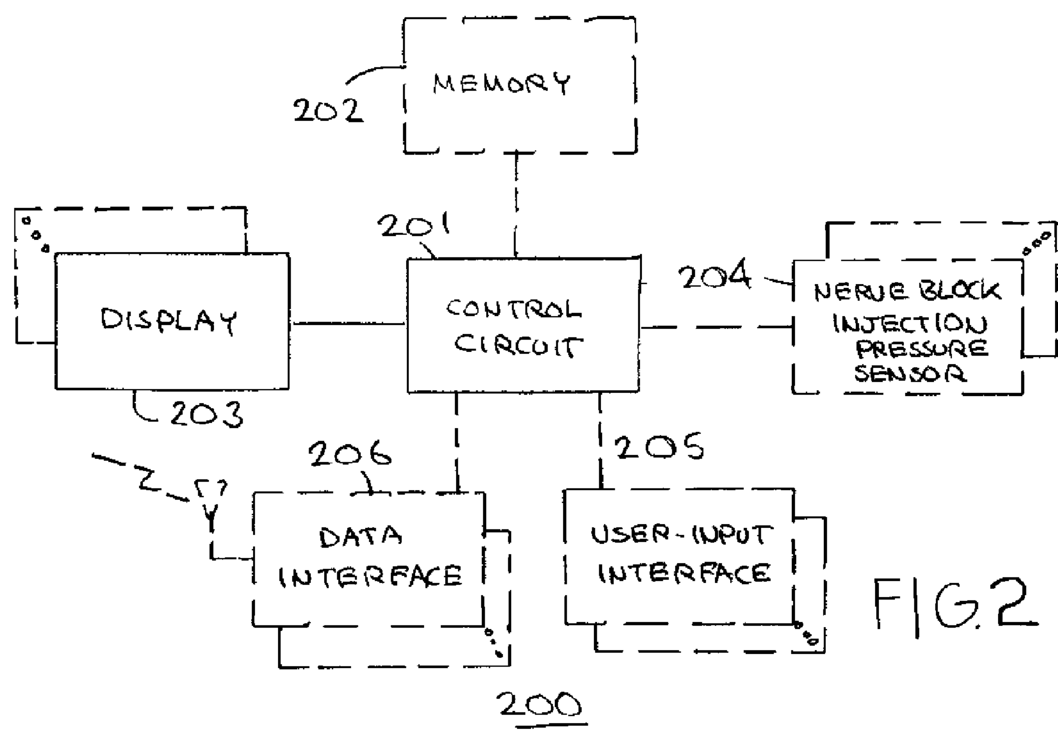
FIG. 2 comprises a block diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit that operably couples to a display and to a nerve block injection pressure sensor provides a display of both a current nerve block injection pressure value and a current nerve block injection pressure categorical range. That categorical range can comprise, for example, one of a plurality of available categorical ranges that may be visually differentiated from one another by color if desired.

By one approach the control circuit can also detect a maximum nerve block injection pressure value (and/or calculate a mean nerve block injection pressure value) as corresponds to a given monitored nerve block injection procedure. In such a case such information can also be displayed if desired.

By another approach, in lieu of the foregoing or in combination therewith, the control circuit can detect negative nerve block injection pressure events. Such events, in turn, can serve to identify aspiration events (i.e., events that pertain to reversing the flow of the anesthetic fluid) and thereby facilitate a count of aspiration events during the course of a given nerve block injection procedure. Such a count, in turn, can help to prompt as well as document compliance with recommendations for medico-legal documentation and communication among clinicians in these regards.

By another approach, again in lieu of the foregoing or in combination therewith, the control circuit can serve to prompt a "time out" procedure before the actual nerve block injection procedure during which, for example, the service providers who are to administer the nerve block (alone or in combination with others such as an attending surgeon, the patient themselves, or others as desired) can check and confirm the appropriate laterality for the nerve block. This laterality can refer, for example, to either the left side of the patient's body or the right side of the patient's body, upper versus lower extremity, and and so forth. Failure to perform a time out procedure can lead to a placement of a nerve block and/or surgery on the wrong side or part of the body and patient harm. Although time-out is required in many hospitals, it may be forgotten in the busy operating room environment and blocks on the wrong side of the body continue to occur and be reported in the literature.

So configured, various items of information regarding nerve block injection pressures can be provided to various persons, both at the time of administering the nerve block and subsequent to administering the nerve block. Such information can help to inform the person or persons responsible for administering the nerve block with respect to whether the anesthetic is being administered in an unsuitable location at the time of so administering the anesthetic. Such information can also help to provide an auditable historical record regarding many of the details of administering an anesthetic in a given procedure.

These teachings are highly flexible in practice. For example, the aforementioned display can be co-located with the control circuit and/or with (or immediately near) the nerve block needle. So configured, at least some information of interest can appear on the hub of the nerve block needle so as to be in the view path of the clinician's line of vision during the performance of the procedure.

If desired, however, the display (or an additional display) can be remotely located from the control circuit and/or the nerve block needle. For example, a large flat-screen display that is available for use in the facility/room where the nerve block is being administered can serve in these regards. As yet another example of the flexibility of these teachings, the display (or an additional display) can even be remote from the foregoing facility to thereby permit remote real-time monitoring of the nerve block injection procedure by one or more persons located in another floor of the same building, in another building, in another city, or even in another country or on another continent.

The present teachings are also highly scalable and will accommodate a wide range of display sizes, pressure sensors, form factors, and so forth. To a very real extent the enabling apparatus can be as small, or as large, as may be desired to suit the needs of and/or the opportunities provided by a given application setting. These teachings can be carried out in a highly economical manner and are readily applied with many existing nerve block administration technologies and methods. Accordingly, the present teachings can serve to greatly leverage many existing nerve block administration techniques and hence help to encourage the continued viability and vitality of such techniques.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example it will be presumed here that a control circuit of choice carries out this process 100. Again for the sake of example it will be further presumed that this control circuit operably couples to both a display and to a nerve block injection pressure sensor.

Referring momentarily to FIG. 2, such a control circuit 201 may comprise a part of a corresponding apparatus 200. Such a control circuit 201 can comprise a fixed-purpose hard-wired platform or can comprise a partially or wholly programmable platform. These architectural options are well known and understood in the art and require no further description here. This control circuit 201 is configured (for example, by using corresponding programming as will be well understood by those skilled in the art) to carry out one or more of the steps, actions, and/or functions described herein.

If desired, the control circuit 201 can operably couple to an optional memory 202. The memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

This memory 202 can serve, for example, to store the detected and/or calculated data described herein. This memory 202 can also serve to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

In this example the control circuit 201 operably couples to at least one display 203. As with the memory 202, this display 203 may be local to the control circuit 201 (or the physical bounds and constraints of the apparatus 200 itself) or may be remote therefrom. When remote, by one approach the display can comprise a flip-on component that the clinician can easily attach where desired (for example, to the patient, to the bed, and so forth). By another approach the display can be configured to easily mount to a vertical pole (the likes of which are frequently available in an operating room).

The display 203 may operably couple to the control circuit 201 using any of a variety of channels including both wireless channels as well as non-wireless channels. These teachings will accommodate any of a wide variety of display technologies including simple alphanumeric displays, monochromatic or multi-color displays, and so forth. As display technologies are very well known in the art and as the present teachings are not overly sensitive to any particular choices in these regards, further elaboration will not be provided here in these regards for the sake of brevity.

As noted above it is presumed here for the sake of illustration that the control circuit 201 also operably couples to at least one nerve block injection pressure sensor 204. Such sensors are known in the art. These teachings will accommodate, for example, using a potentiometer or the like to respond to the physical displacement of a mechanical member that moves to various positions as a function of the pressure being monitored. As another example, various pressure-sensitive electrical components are known in the art that can serve in these regards as well. In many application settings it will serve well to place the nerve block injection pressure sensor 204 in-stream between the needle and the syringe body (or other corresponding fluid-containment or fluid-delivery vessel). (If desired, the sensor 204 can include a disposable fluid path to facilitate sterile reuse of the sensor 204.)

Also in this illustrative example the control circuit 201 operably couples to both an optional user-input interface (or interfaces, as desired) 205 and one or more data interfaces 206. The user-input interface 205 can comprise any of a wide variety of interfaces including but not limited to electromechanical buttons and switches, virtual buttons (via, for example, a touch-sensitive display), a limited or full character set keyboard, a cursor-control device, a voice-based interface, and so forth. The data interface 206 can similarly comprise any of a wide variety of interfaces including wireless interfaces (such as but not limited to Bluetooth™-compatible transceivers and so forth) and non-wireless interfaces (such as but not limited to the ubiquitous Universal Serial Bus (USB) interface and so forth).

So configured, such a control circuit 201 can receive information regarding injection pressures during nerve block performance and can store some or all of that information and/or calculate other values based upon that received information. Some or all of the foregoing information can be displayed and/or transmitted as desired with some or all of the foregoing functionality and capabilities being responsive, in whole or in part, to inputs from a user of the apparatus 200.

Referring again to FIG. 1, such a control circuit 201 can begin (at 101) to monitor nerve block injection pressures as occur during a given nerve block injection procedure. By one approach this activity begins in response to the user activating a "start" command via, for example, the aforementioned user input interface 205. By one approach, if desired, this step can include resetting the monitoring activity to thereby clear previously-collected data from the monitoring of a previous procedure. (If desired, a separate and discrete user-input interface opportunity, such as a dedicated reset button, can serve to so reset the control circuit 201 in these regards.)

By another approach, in lieu of the foregoing or as a supplement thereto, this monitoring process can begin in an automated fashion. For example, the pressure sensor 204 can be monitored in a general way and if and when a given rise in pressure occurs (for example, an increase of 4 psi or more over a period of no more than, say, 5 seconds) the monitoring at 101 can begin as regards the start of a corresponding nerve block injection procedure.

If desired, upon beginning such a process 100 (or shortly thereafter) the control circuit 201 can effect a procedural time out to thereby prompt the user to conduct a determination and/or confirmation of the laterality of the nerve block injection. Such a time out is already a recommended procedure in many practice jurisdictions and such an accommodation by the control circuit 201 can help to prompt compliance with such a recommendation. By one approach, for example, the user can indicate determination/confirmation of the laterality decision via the user-input interface 205. This confirmation of laterality requirement and/or a general time out procedure can be communicated to the clinician in any of a multitude of ways, including via visual, audible, haptic, or even via nonresponsiveness until the clinician confirms/activates the device in a manner to indicate that the time out procedure is done.

If desired, at 103 the control circuit 201 can optionally monitor a duration of time for injection and or procedure as corresponds to the monitored nerve block injection procedure. The information provided can be used both for the purpose of research and medico-legal documentation in everyday clinical practice. By one approach, for example, this duration can start when beginning the aforementioned monitoring at 101 and can conclude with the conclusion of the procedure as described below. In such a case, if desired, this process 100 will also accommodate displaying that duration of time. By one approach this can comprise displaying the cumulative duration in real-time as that duration incrementally increases (for example, second by second). By another approach this process 100 will accommodate only providing a final duration value at the conclusion of the procedure if desired.

In any event, at 104 this process 100 provides for monitoring nerve block injection pressure via the nerve block injection pressure sensor 204. For many application settings it will suffice to monitor the nerve block injection pressure by sampling data from the nerve block injection pressure sensor 204 on some periodic basis (such as, for example, every 10 milliseconds, every 100 milliseconds, every 500 milliseconds, or per some other period of choice).

By one approach the control circuit 201 can store each and every sensor reading. By another approach the control circuit 201 can store representational data (such as, for example, an average value for all of the sensor readings for some contiguous period of time such as all readings for each 2 seconds of time). By yet another approach, the control circuit 201 may be configured to only use a most current reading value and to then discard prior readings.

If desired, in addition to the foregoing the control circuit 201 can be optionally configured to, at 105, detect a maximum nerve block injection pressure value as occurs during the monitored nerve block injection procedure. In addition, or in lieu thereof, the control circuit 201 can be optionally configured to calculate one or more values that represent some aggregated view of the monitored sensor values. For example, and as shown at 105, this can comprise calculating a mean nerve block injection pressure value as corresponds to the monitored nerve block injection procedure.

At 106, the control circuit 201 displays the current nerve block injection pressure value. By one approach the displayed nerve block injection pressure value can comprise a displayed integer value (which would suffice for many application settings). By another approach, if desired, the displayed value could include decimal places or fractions as well. It would also be possible to display this current nerve block injection pressure value via, for example, a representation of an analog meter, a bar-based scale, and so forth.

In this particular illustrative example the control circuit 201 also co-displays a current nerve block injection pressure categorical range as corresponds to that current nerve block injection pressure value. By one approach there may be three such categorical ranges that respectively represent, for example, a below-normal range of nerve block injection pressure values, a normal range of nerve block injection pressure values, and an above-normal range of nerve block injection pressure values. If desired, and to facilitate readily visually distinguishing one categorical range from another, each of the three categorical range may have a different correspond color (such as white for the below-normal range, green for the normal range, and red for the above-normal range).

By co-displaying such information the user can readily see both a categorical representation regarding the normality of the current pressure along with the actual value of the current pressure. Both of these indicators, alone as well as in tandem, can be helpful to the user when making decisions based upon whether the needle is properly located in the patient.

At 107 the control circuit 201 will also optionally accommodate displaying the aforementioned maximum nerve block injection pressure value and/or the aforementioned mean injection pressure value. These can be values that represent currently-calculated values notwithstanding that the procedure itself has not yet completed, or, if desired, these values may only be displayed upon concluding the procedure.

If desired, the ability of the control circuit 201 to monitor nerve block injection pressures over time can be leveraged in other optional ways. As one example, at 108 the control circuit 201 can detect negative nerve block injection pressure events. This activity can comprise, for example, detecting that a currently-measured nerve block injection pressure value is less than a just-preceding nerve block injection pressure value. The control circuit 201 can then count at least some of these negative nerve block injection pressure events (for example, those negative nerve block injection pressure events that persist for at least some minimal amount of time such as 150 milliseconds, 300 milliseconds, or some other duration of relevance and interest) as aspiration events.

As used herein, the expression "aspiration events" will be understood to refer to occasions when the technician administering the anesthesia reverses the syringe plunger. Aspiration is usually recommended when administering nerve blocks as part of assuring, for example, that the needle is not positioned in a vein or artery. In fact, many recommended procedures specify aspirating at least a specific number of times (such as five times) during the course of a single procedure.

The control circuit 201 can display this aspiration event count as desired. By one approach this can comprise showing a real-time count of how many aspiration events have occurred so far during a present nerve block injection procedure. By another approach this can comprise displaying the final accumulative count at the conclusion of the procedure monitoring process.

Eventually, the control circuit 201 can conclude the above-described monitoring at 109. By one approach the control circuit 201 takes this action in response to the user entering a "stop" instruction 110 via the user-input interface 205. By another approach, the control circuit 201 takes this action as an automatic response to the monitored nerve block injection pressure having dropped to some minimal value for some predetermined period of time.

In addition to displaying various items of information as described above, by one optional approach the control circuit 201 can also transmit information regarding nerve block injection pressure at 111 (via, for example, the above-described data interface 206). This transmission can comprise a so-called push transmission, a so-called pull transmission, or some combination thereof as desired. So configured, for example, a centralized record can be maintained for such information. Those skilled in the art will recognize and understand that a comprehensive record regarding the administration of a nerve block can be valuable to facilitate a procedures-compliance audit and/or to facilitate and instantiate the defense of a claim of malfeasance regarding the nerve block procedure.

By one approach this transmission of information occurs in response to the user having entered a "send" instruction 112 or the like via the user-input interface 205. By another approach this transmission of information can occur automatically in response to concluding the monitoring portion of the process 100. When the transmission comprises a pull-based transmission, the transmission can occur in response to receiving a request for the information (via, for example, the data interface 206).

Figure 3:
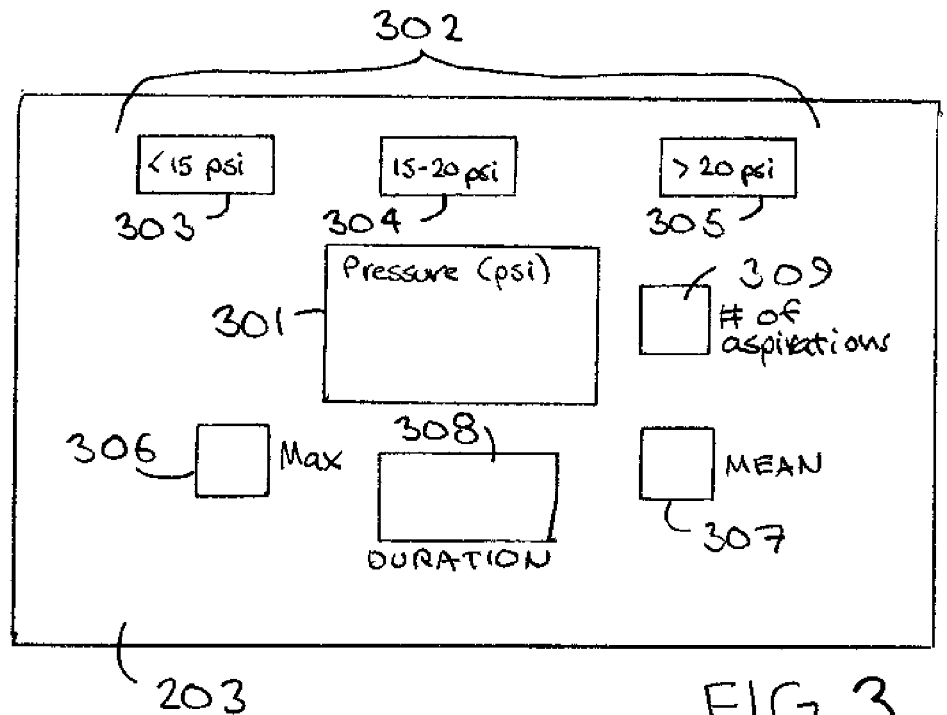
FIG. 3 comprises a display screen shot as configured in accordance with various embodiments of the invention.

The above-described process 100 provides for the display of any of a variety of informational items. FIG. 3 provides one illustrative example of such a display 203. It will be understood that the specifics of this example are intended to serve only in an illustrative capacity and are not intended to suggest any particular limitations in these regards.

In this illustrative example the display 203 includes a first display area 301 where real-time pressure values can be displayed. The top of the display 203 includes a plurality of categorical range indicators 302. In this particular example there are three such categorical range indicators 302 consisting of a below-normal range of nerve block injection pressure values 303, a normal range of nerve block injection pressure values 304, and an above-normal range of nerve block injection pressure values 305.

One display area 306 serves for the above-described maximum nerve block injection pressure value while another display area 307 serve for the above-described mean nerve block injection pressure value. In this illustrative example the aforementioned duration information for a currently-monitored procedure is accommodated by yet another display area 308. Finally, the above-mentioned count of the number of detected aspirations is accommodated by its own display area 309.

Figure 4:
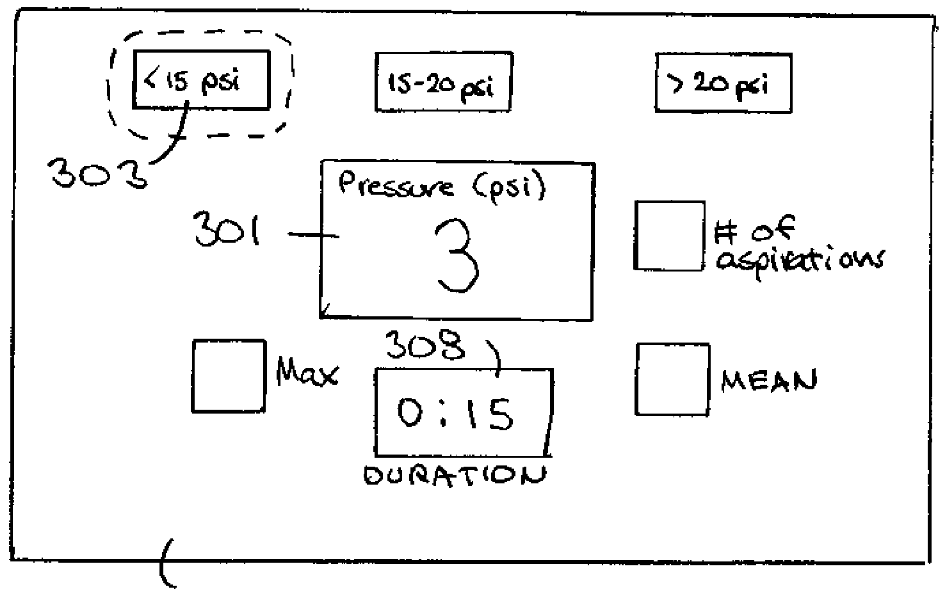
FIG. 4 comprises a display screen shot as configured in accordance with various embodiments of the invention.

FIGS. 4-8 provide some snapshots of how such a display 203 might look during the course of a given nerve block injection procedure per the above-described process 100. In FIG. 4 the procedure has only just begun. The present duration is shown to be fifteen seconds and the current nerve block injection pressure value is shown to be three PSI. Because three PSI is less than the normal range, the below-normal range indicator 303 is highlighted (for example, by illuminating this indicator 303 using the color white). (In this illustrative example, the maximum and mean values as well as the count of aspirations are not shown until the procedure concludes.)

Figure 5:
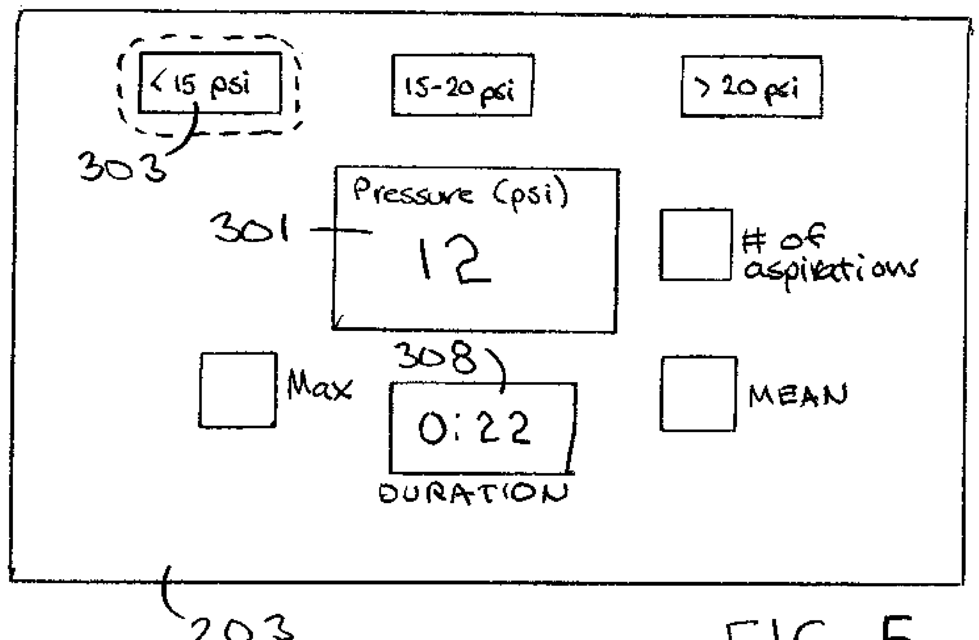
FIG. 5 comprises a display screen shot as configured in accordance with various embodiments of the invention.

In FIG. 5 the procedure is a few seconds further along. The duration has been updated to twenty-two seconds and the pressure indicator now reads twelve PSI. This pressure reading is still below normal and hence the below-normal range indicator 303 remains highlighted.

Figure 6:
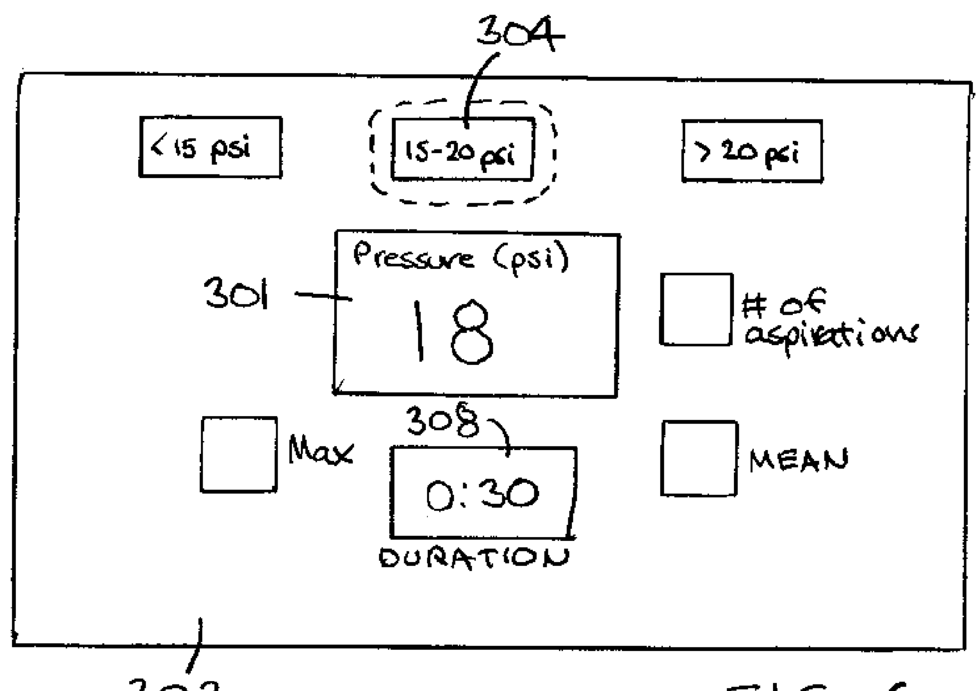
FIG. 6 comprises a display screen shot as configured in accordance with various embodiments of the invention.

In FIG. 6, at thirty seconds into the procedure, the pressure has reached eighteen PSI. Since this value is within the normal range (which is, in this example, fifteen to twenty PSI) the normal range indicator 304 is now highlighted (for example, by illuminating this indicator 304 using the color green).

Figure 7:
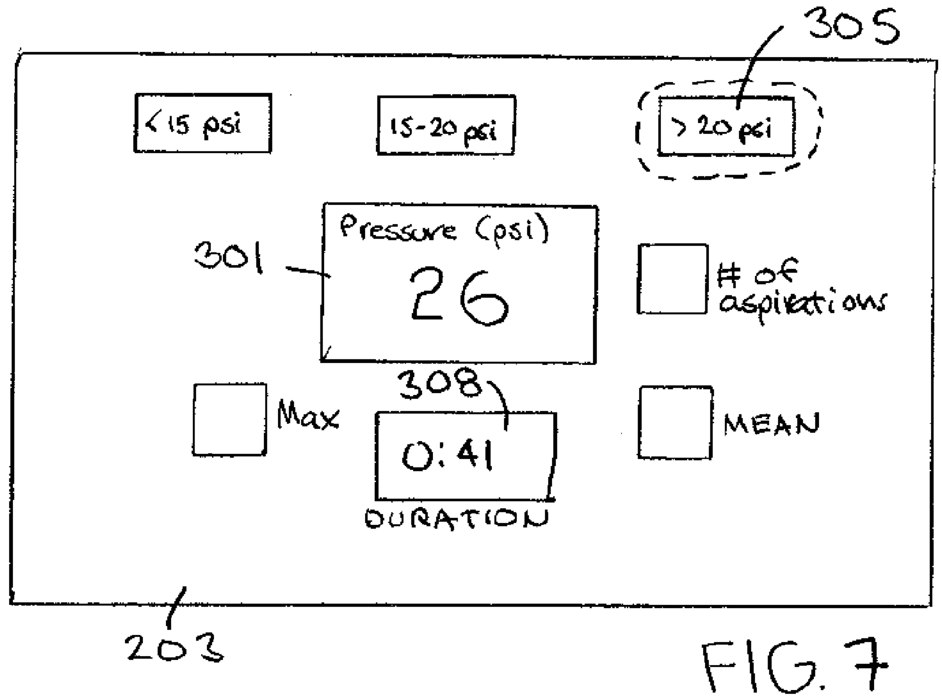
FIG. 7 comprises a display screen shot as configured in accordance with various embodiments of the invention.

In FIG. 7, at forty-one seconds into the procedure, the pressure reaches twenty-six PSI. Since this value exceeds the normal range the above-normal range indicator 305 is now highlighted (for example, by illuminating this indicator 305 using the color red).

Figure 8:
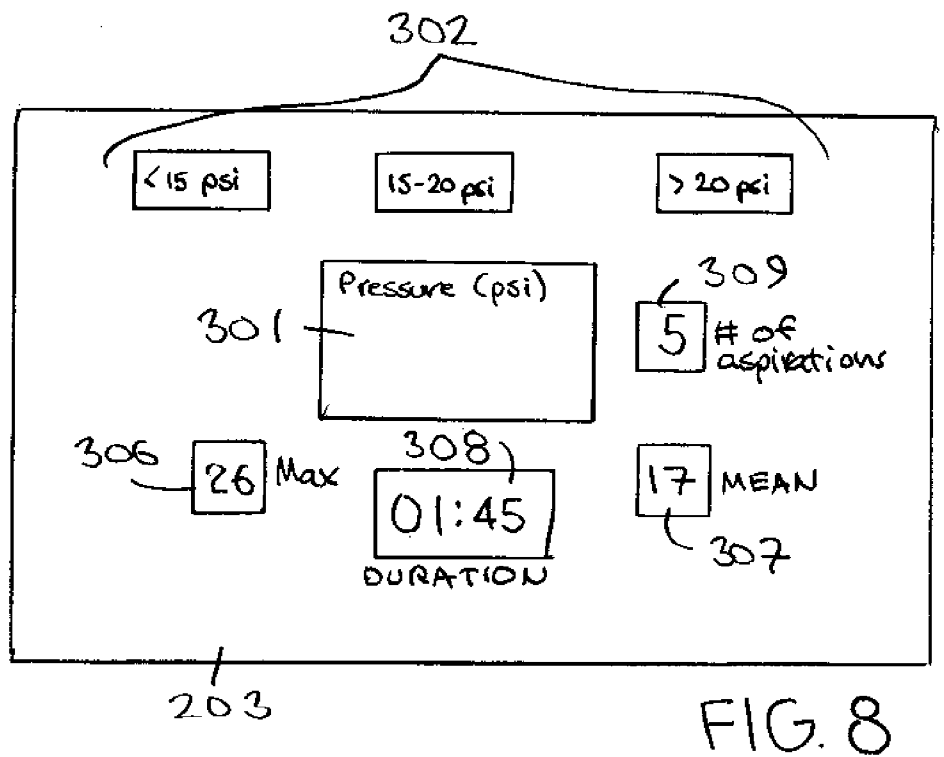
FIG. 8 comprises a display screen shot as configured in accordance with various embodiments of the invention.

In FIG. 8 the procedure has concluded as has the pressure monitoring. Accordingly the real-time pressure value display area 301 is blank and none of the categorical range indicators 302 are highlighted. The total duration is shown to be one minute and forty-five seconds. In addition, the maximum detected nerve block injection pressure value is shown as twenty-six PSI, the mean value is shown to be seventeen PSI, and a total of five aspirations are shown as having been detected.

Figure 9:
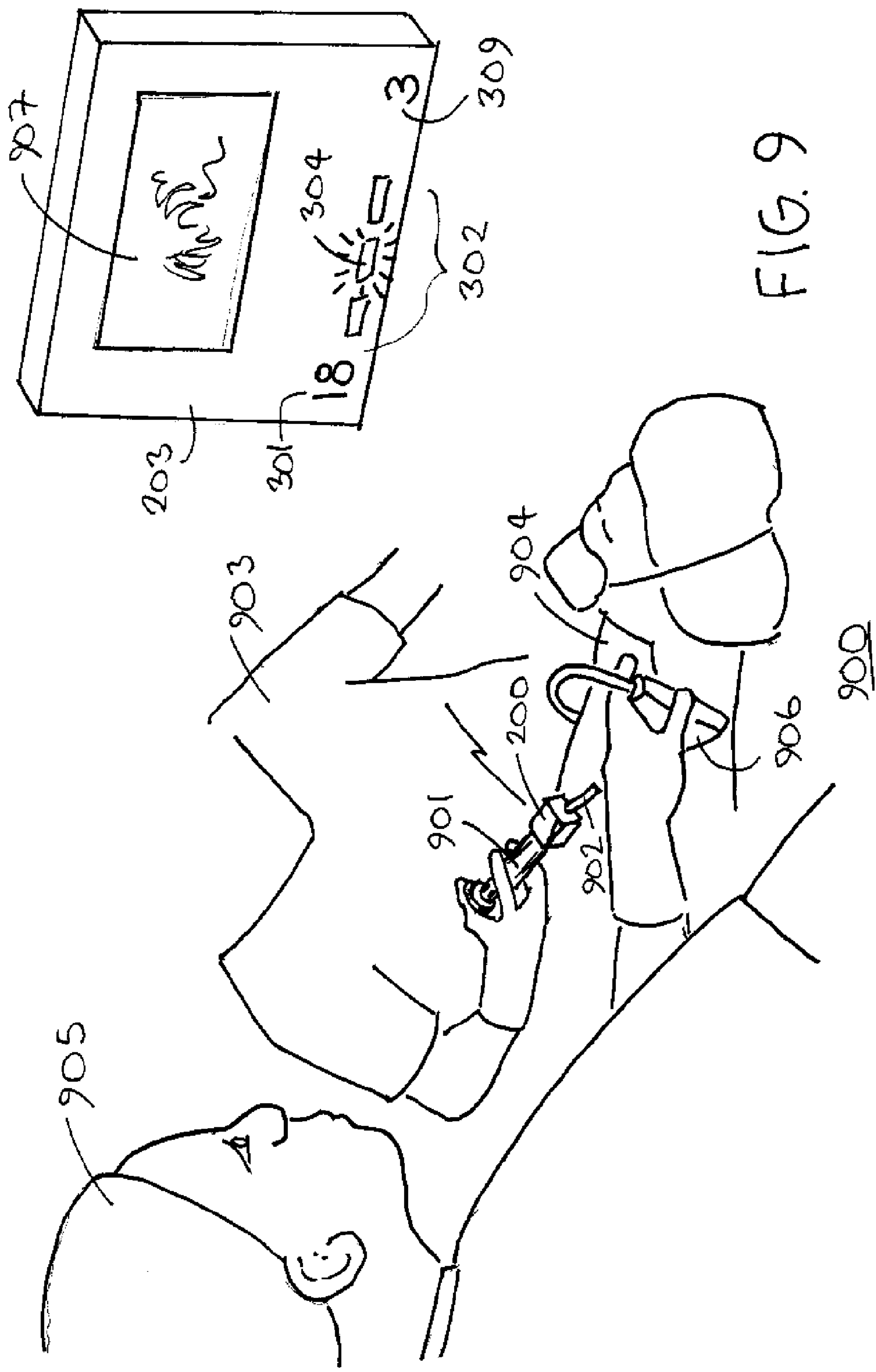
FIG. 9 comprises a perspective view as configured in accordance with various embodiments of the invention.

As noted earlier these teachings are highly flexible in practice and will readily accommodate a wide variety of variations. FIG. 9 provides one illustrative example in these regards. In this example a patient 904 receives a nerve block while at a given facility 900 (such as an operating room at a hospital or other medical-services facility). A first technician 903 administers the syringe 901 while a second technician 905 manipulates an ultrasound transducer 906 in accordance with well-understood prior art technique as part of monitoring the procedure.

In this example, the above described apparatus 200 (and hence the above described control circuit 201 and also inclusive of the nerve block injection pressure sensor 204) is disposed in-line between the syringe 901 and the needle 902. Also in this example control circuit 201 operably couples to the display 203 via a wireless link.

The display 203 itself comprises a flat-screen display that is physically remote from the control circuit 201 and that is located, for example, a few feet away from the control circuit 201. This display 203 presents, in this example, the abovementioned real-time pressure value 301 and the categorical range indicators 302 along with a real-time cumulative count of the number of detected aspiration events 309. (In this particular example the current pressure is eighteen PSI and therefore the normal range indicator 304 is highlighted as compared to the remaining categorical range indicators 302.)

In addition, the display 203 also presents the ultrasound display 907 as corresponds to the ultrasound transducer 906. So configured, the persons administering the nerve block have a great deal of objective information visually available in an aggregated, concise, intuitive, and convenient manner. The display 203 can of course accommodate other information as well as desired. Examples include, but are not limited to, nerve stimulation information (such as information regarding current delivery, current intensity, and disconnect/electrical failure), blood pressure information, heart-monitor information, and so forth.

So configured, the administration of a nerve block can benefit in a number of ways. The ready availability of useful, objective, accurate, and readily perceived and understood information regarding nerve block injection pressures offers a depth of understanding that is presently unavailable. Similarly, the ability to store a variety of data points regarding pressure-based events and performance on a procedure-by-procedure basis greatly increases the opportunities for meaningful quality evaluation and control. Furthermore, these teachings offer unique opportunities to help prompt behaviors that comply with acknowledged (and even required) best practices.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As one example in these regards, the background color for the current pressure reading (or the color for the pressure reading value characters themselves) can serve as the aforementioned categorical range indicators. As another example, these teachings will readily accommodate sensing information regarding the quantity of injected fluid and displaying such information on the display 203. This could comprise, for example, displaying the currently injected fluid as a given number of milliliters. Even when not displayed, such information (particularly if timestamped) can be useful with respect to more fully documenting the specifics of the procedure.

I claim:

1. An apparatus comprising:

a display, a syringe comprising a syringe body, a syringe plunger, and a needle;

a control circuit operably coupled to the display and to a nerve block injection pressure sensor, the pressure sensor disposed in-line between the syringe body and the needle and configured to sense the injection pressure of a hand-administered nerve block injection on relative axial movement of the syringe plunger to the syringe body, the control circuit configured to provide, via the display, both a current nerve block injection pressure value and a current nerve block injection pressure categorical range.

2. The apparatus of claim 1 wherein the current nerve block injection pressure value as shown on the display comprises an integer value.

3. The apparatus of claim 1 wherein the current nerve block injection pressure categorical range as shown on the display comprises a highlighting of one of a plurality of categorical ranges.

4. The apparatus of claim 3 wherein the plurality of categorical ranges comprise a total of three categorical ranges.

5. The apparatus of claim 4 wherein the three categorical ranges respectively represent a first range of nerve block injection pressure values, a second range of nerve block injection pressure values that is below the first range of nerve block injection pressure values, and a third range of nerve block injection pressure values that is above the first range of nerve block injection pressure values.

6. The apparatus of claim 4 wherein the three categorical ranges each have a different corresponding color.

7. The apparatus of claim 1 wherein the control circuit is further configured to detect via the nerve block injection pressure sensor negative nerve block injection pressure and to count at least some detections of negative nerve block injection pressure as an aspiration event.

8. The apparatus of claim 7 wherein the control circuit is further configured to present, via the display, an aggregated count of the aspiration events.

9. The apparatus of claim 1 wherein the control circuit is further configured to display a duration of time which corresponds to a monitored nerve block injection procedure.

10. The apparatus of claim 1 wherein the control circuit is further configured to:

detect a maximum nerve block injection pressure value as occurs during a monitored nerve block injection procedure;

present, via the display, the maximum injection pressure value.

11. The apparatus of claim 1 wherein the control circuit is further configured to:

calculate a mean nerve block injection pressure value as corresponds to a monitored nerve block injection procedure;

display, via the display, the mean injection pressure value.

12. The apparatus of claim 1 further comprising:

a data interface operably coupled to the control circuit;

wherein the control circuit is configured to transmit information regarding nerve block injection pressure values as occurs during a monitored nerve block injection procedure.

13. The apparatus of claim 12 wherein the data interface comprises at least one of:

a wireless data interface; and a non-wireless data interface.

14. The apparatus of claim 1 further comprising:

a user-input interface operably coupled to the control circuit;

wherein the control circuit is configured to respond, at least in part, to the user-input interface by resetting monitoring of a monitored nerve block injection procedure.

* * * * *

UNITED STATES PATENT AND TRADEMARK OFFICE

CERTIFICATE OF CORRECTION

PATENT NO. : 9,662,459 B2
APPLICATION NO. : 13/723611
DATED : May 30, 2017
INVENTOR(S) : Admir Hadzic It is certified that error appears in the above-identified patent and that said Letters Patent is hereby corrected as shown below:

In the Claims

Claim 1, Column 10, Line 6; change "display," to -- display; --.

Signed and Sealed this
Nineteenth Day of September, 2017

Joseph Matal

Joseph Matal
*Performing the Functions and Duties of the
Under Secretary of Commerce for Intellectual Property and
Director of the United States Patent and Trademark Office*